United States Patent [19]

Maslanka

[11] Patent Number: 4,646,751
[45] Date of Patent: Mar. 3, 1987

[54] BIOPSY FORCEPS

[75] Inventor: Harald Maslanka, Tuttlingen, Fed. Rep. of Germany

[73] Assignee: Diener Verwaltungs-und Beteiligungsgesellschaft m.b.H., Fed. Rep. of Germany; a part interest

[21] Appl. No.: 735,313

[22] Filed: May 17, 1985

[30] Foreign Application Priority Data

May 18, 1984 [DE] Fed. Rep. of Germany ... 8415222[U]

[51] Int. Cl.[4] .............................................. A61B 17/32
[52] U.S. Cl. ..................................... 128/751; 128/321
[58] Field of Search .......... 128/6, 7, 8, 303.14–303.17, 128/321–324, 673–675, 749–758

[56] References Cited

U.S. PATENT DOCUMENTS

| | | | |
|---|---|---|---|
| 1,294,284 | 2/1919 | Logeman | 128/321 |
| 1,845,727 | 10/1930 | Slaughter | 604/267 |
| 2,031,682 | 2/1936 | Wappler et al. | 128/303.15 |
| 3,606,878 | 10/1968 | Kellogg, Jr. | 128/753 |
| 3,850,175 | 11/1974 | Iglesias | 128/7 |
| 3,964,468 | 6/1976 | Schulz | 128/751 |
| 4,167,943 | 9/1979 | Banko | 128/305 |

FOREIGN PATENT DOCUMENTS 2332743 11/1975 France ............................... 128/753

Primary Examiner—Kyle L. Howell
Assistant Examiner—Randy Citrin
Attorney, Agent, or Firm—Watts, Hoffmann, Fisher & Heinke

[57] ABSTRACT

An improved flexible biopsy forceps with cleaning port for introducing cleansing fluid into the interior of the forceps.

6 Claims, 2 Drawing Figures

BIOPSY FORCEPS

TECHNICAL FIELD

This invention relates generally to flexible biopsy instruments and more particularly to an improved flexible biopsy forceps having a cleaning port.

BACKGROUND ART

Typical flexible forceps used for gastroscopy, bronchoscopy and the like comprise an operating cable, a pincer mounted at the distal end of the operating cable and a manual operating device at the proximal end of the operating cable. The operating cable of a flexible biopsy forceps is covered with a cable jacket having one end fixed to the manual operating device and its other end to the pincer mounting. Flexible forceps are ideally constructed as an inseparable unit to give the forceps stability. Inseparable instruments also cost less to manufacture than instruments assembled from separate components.

While inseparable instruments have greater stability and cost less to make than instruments which can be disassembled, they are difficult to clean. During use the inside of the cable jacket, the operating cable, the pincer mounting and the pincers become soiled. The sensitive scissor action pincers, which are housed within a slotted cylindrical pincer mounting, become blocked with material that is not easily removable by soaking and the instrument becomes unusable.

DISCLOSURE OF INVENTION

The present invention provides an improved flexible biopsy forceps which have the stability and cost advantages of inseparable forceps and which have a cleaning port for easy and complete cleansing of the interior of the instrument.

More particularly, the invention is an improvement in a flexible biopsy forceps of the type including a cable jacket, a pincers at the distal end of the jacket, an operating cable attached to the pincers and extending within the jacket, and an operating assembly attached to the proximal end of the cable. In accordance with the invention the operating assembly includes a connecting rod, a socket and a tubular member wherein the socket defines a space between itself and the tubular member, the connecting rod extends through the socket and is attached to the operating cable, the socket is connected to the cable jacket, and the socket has at least one socket passage connecting the space between the socket and the tubular member with the interior of the socket; the socket is housed within the tubular member which has an irrigation opening to provide communication with the interior of the socket by way of the socket passage or passages openings; and a fluid inlet tube carried by the tubular member for introducing cleansing fluid under pressure into the interior of the socket and the jacket for cleaning the operating cable and pincers.

As distinguished from prior art arrangements, the operating assembly is provided with a cleaning port for introducing cleansing fluid into the interior of the instrument at the proximal end in such a manner that the fluid is prevented from escaping at the proximal end and is directed toward the distal end.

Other advantages and a more complete understanding of the invention will be had from the following detailed description when taken in conjunction with the accompanying drawings.

BEST MODE FOR CARRYING OUT THE INVENTION

Figure 1:
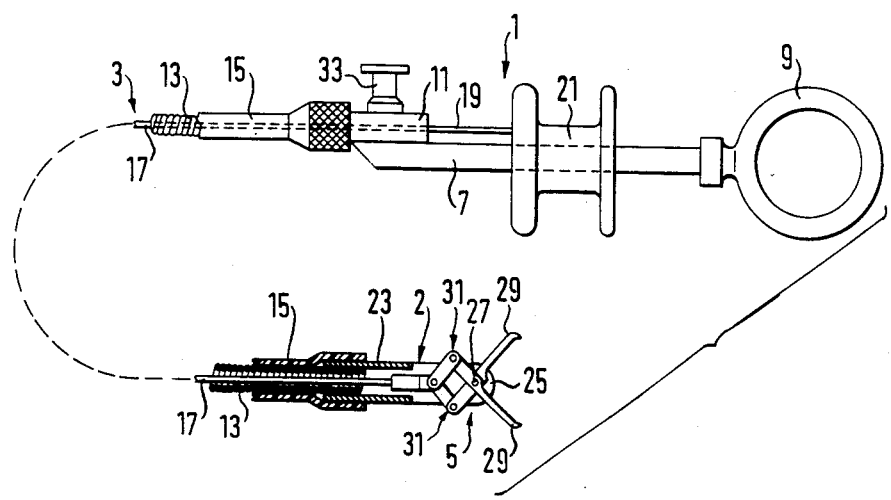
FIG. 1 is a side view of the flexible biopsy forceps which includes a cross-sectional view of the pincers and pincer-mounting.

Referring to FIG. 1, there is shown the operating assembly 2, a flexible cable assembly 3 and a forceps 5.

The operating assembly 2 is composed of a tubular member 11 mounted on a guide shaft 7, which bears a slidable finger grip 21 and a thumb ring 9. The finger grip 21 is connected to an operating cable 17 by a coupling rod 19 which passes through the tubular member 11. A fluid inlet tube 33 is connected to the tubular member 11. The fluid inlet tube 33 may be a Luer-lock or the like.

The flexible cable assembly 3 is composed of a cable jacket 13 and the operating cable 17. The cable jacket 13 is attached to the operating assembly 2 at the proximal end and the forceps 5 at the distal end by means of an outside plastic covering 15.

The forceps 5 are composed of jaws 29, a pincer mounting 25, a pivot 27, lever arms 31, and a pincer mounting collar 23. The lever arms 31 are connected to the operating cable 17. A pincer mounting collar 23 is connected to the cable jacket 13 by the outside plastic covering 15. When the thumb grip 9 and the finger slide 21 are moved toward each other, the jaws 29 are closed. When the thumb grip 9 and finger slide 21 are moved away from each other, the jaws 29 are opened.

Figure 2:
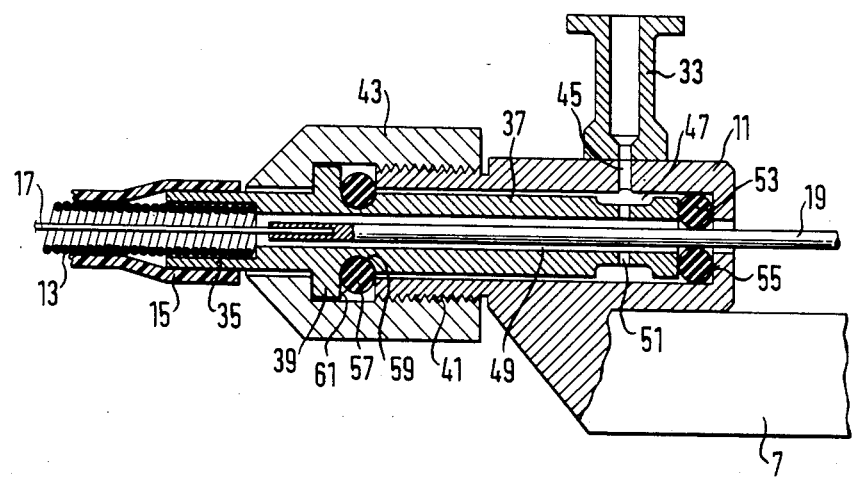
FIG. 2 is a cross-sectional view of the operating assembly embodying the cleaning port.

Referring to FIG. 2 there is shown a cross-sectional view of the operating assembly 2. In accordance with the present improvement, the operating assembly 2 comprises a tubular member 11, a socket 37, and a fluid inlet tube 33.

The fluid inlet tube 33 communicates with the inside of tubular member 11 by an orifice 45, which is located adjacent to a ring groove 47 formed on the outer surface of the socket 37. Located within the ring groove 47 are one or more openings 51 so that there is communication between the ring groove 47 and a ring space 49, which is sealed at the proximal end of the tubular member 11 by a sealing ring 53 located between the proximal end of the socket 37 and a ring shoulder 55 of the tubular member 11. The sealing ring 53 tightly encloses the coupling rod 19 to prevent cleansing fluid from escaping from the proximal end of the tubular member 11. The ring space 49 communicates with the inside of the cable jacket 13. The cable jacket 13 is held inside the socket 37 by means of a socket end 35. The cable jacket 13 is sealed to the socket end 35 by the outside plastic covering 15. The cable jacket 13 encloses the operating cable 17 which is attached to the coupling rod 19 extending through the socket 37. The distal end of the socket 37 bears a ring shoulder 39 extending radially outward which, by means of a coupling nut 43 screwed onto the outer threading 41 of tubular member 11, serves to hold the socket 37 against the tubular member 11. The proximal side of the ring shoulder 39 has a ring shoulder surface 61 and a ring groove 59 to accommodate a sealing ring 57. The sealing ring 57 seals the end surfaces of the tubular member 11 against the ring shoulder surface 61 of the socket 37.

To clean the forceps a cleansing solution is introduced into the instrument by attaching a hose, syringe or the like to the fluid inlet tube 33. A syringe can be securely attached to the fluid inlet tube 33 if the fluid inlet tube is a Luer-lock or the like. Since the cable jacket 13 and the operating cable 17 are elongated, it is desirable to introduce the cleansing solution under pressure so that the solution can be forced through the instrument to dislodge any material trapped within the cable jacket 13 and the forceps 5. To ensure that the cleansing solution reaches the forceps 5 under pressure and does not leak from the operating assembly 2, the invention provides for a sealing ring 53 which prevents leakage around the coupling rod 19 and another sealing ring 57 which prevents leakage around the coupling nut 43.

I claim:

1. In a flexible biopsy forceps of the type including a cable jacket, a pincers connected to the distal end of the cable jacket, an operating assembly connected to the proximal end of the cable jacket, an operating cable attached to the pincers and the operating assembly and being movable within and extending through the cable jacket and operating assembly, the improvement wherein the operating assembly includes:
   a tubular member;
   a hollow socket having a radial passage within said tubular member and attached at a distal end to the cable jacket;
   a connecting rod extending through the socket and attached at a distal end to the operating cable;
   a first sealing ring within the tubular member in engagement with the connecting rod and the socket;
   a second sealing ring encircling the socket and in engagement with the tubular member;
   a capnut threaded onto the distal end of the tubular member, said capnut having socket engagement means for engaging said socket in said tubular member;
   said socket and said tubular member defining a first annular space between the socket and the tubular member, and said socket and said connecting rod defining a second annular space between the socket and the connecting rod, said first and second spaces in communication with the radial passage of the socket and further in communication with the interior of the cable jacket; and
   said tubular member having an irrigation opening providing communication with the interior of the cable jacket for introducing cleaning fluid under pressure.

2. The improvement as claimed in claim 1 wherein said first annular space is further defined by a reduced diameter annular channel on the exterior of said socket.

3. In a flexible biopsy forceps of the type including a cable jacket, a pincers connected to the distal end of the cable jacket, an operating assembly connected to the proximal end of the cable jacket, an operating cable attached to the pincers and the operating assembly and being movable within and extending through the cable jacket and operating assembly, the improvement wherein the operating assembly includes:
   a tubular member;
   a hollow socket partially within said tubular member and attached at a distal end to a proximal end of the cable jacket, said socket having a radially outward projecting ring shoulder and further having a radial passage;
   a capnut threaded onto the distal end of the tubular member, said capnut having an interior annular radial face engaging with a distally facing surface of the radially outward projecting ring shoulder of the socket;
   a connecting rod within the socket and attached at a distal end to the operating cable and further attached at a proximal end to the operating assembly;
   a first sealing ring encircling the socket and abutting a proximally facing surface of the radially projecting ring shoulder of the socket and further abutting a distal end of the tubular member;
   a second sealing ring encircling the connecting rod and abutting a proximal end of the socket and further abutting a proximal end of the tubular member, the tubular member and the socket defining a first annular space between the tubular member and the socket and the socket and the connecting rod defining a second annular space between the socket and the connecting rod, said first annular space in communication with the radial passage of the socket and further in communication with said second annular space, said second annular space in communication with the interior of the cable jacket; and
   said tubular member further having an irrigation opening providing communication with the first annular space, the radial passage and the second annular space for introducing cleaning fluid under pressure into the interior of the cable jacket.

4. The improvement as claimed in claim 3 wherein said first annular space is further defined by a reduced diameter annular channel on the exterior of said socket.

5. In a flexible biopsy forceps of the type including a cable jacket, a pincers connected to the distal end of the cable jacket, an operating assembly connected to the proximal end of the cable jacket, an operating cable attached to the pincers and the operating assembly and movable within and extending through the cable jacket and operating assembly, the improvement wherein the operating assembly includes:
   a tubular member having an inwardly directed radial flange at a proximal end and a first distally facing annular surface at a distal end, said flange defining a second distally facing annular surface and a reduced diameter proximal opening;
   a hollow socket within said tubular member and attached to the proximal end of the cable jacket, said socket having a first proximally facing annular surface at a proximal end and a ring shoulder at a distal end, said ring shoulder projecting radially outward to define a second proximally facing annular surface and a distally facing capnut engagement surface, said socket further having at least one radial passage;
   a capnut threaded onto the distal end of the tubular member, said capnut having an interior annular radial face engaging with the distally facing capnut engagement surface of the socket;
   a connecting rod within said socket and said tubular member and attached to the distal end of the operating cable and projecting from the reduced diameter opening in the tubular member;
   a first sealing ring encircling the socket and abutting the second proximally facing annular surface of the socket and further abutting the first distally facing annular surface of said tubular member;

a second sealing ring encircling the connecting rod and between the socket and the tubular member and abutting the first distally facing annular surface of the tubular member and further abutting the first proximally facing annular surface of the socket;

the tubular member and the socket defining a first annular space between the tubular member and the socket and the socket and the connecting rod define a second annular space between the socket and the connecting rod, said second annular space in commmunication with the interior of the cable jacket;

said tubular member having an irrigation opening to provide communication with the first annular space, the radial passage and the second annular space for introducing cleaning fluid under pressure into the second annular space and the interior of the cable jacket.

6. The improvement as claimed in claim 5 wherein said first annular space is further defined by a reduced diameter annular channel on the exterior of said socket.

* * * * *